United States Patent
Zhang et al.

(10) Patent No.: US 10,363,357 B2
(45) Date of Patent: Jul. 30, 2019

(54) SYSTEM FOR CONTRAST AGENT-BASED MEDICAL IMAGING

(71) Applicant: Siemens Healthcare GmbH, Erlangen (DE)

(72) Inventors: Wen Ju Zhang, Shanghai (CN); Lisa Vallines, Wendlingen (DE); Daniel Lerch, Weilersbach (DE); Carsten Thierfelder, Pinzberg (DE); Yi Mian Wang, Shanghai (CN)

(73) Assignee: SIEMENS HEALTHCARE GMBH, Erlangen (DE)

( * ) Notice: Subject to any disclaimer, the term of this patent is extended or adjusted under 35 U.S.C. 154(b) by 368 days.

(21) Appl. No.: 15/296,066

(22) Filed: Oct. 18, 2016

(65) Prior Publication Data

US 2018/0001016 A1 Jan. 4, 2018

(30) Foreign Application Priority Data

Jun. 30, 2016 (DE) .................... 20 2016 004 185 U

(51) Int. Cl.

| | |
|---|---|
| *A61M 5/00* | (2006.01) |
| *A61B 8/00* | (2006.01) |
| *A61B 5/055* | (2006.01) |
| *A61B 6/00* | (2006.01) |
| *A61B 8/08* | (2006.01) |
| *A61B 6/03* | (2006.01) |
| *A61B 90/50* | (2016.01) |
| *A61B 5/00* | (2006.01) |
| *G01R 33/56* | (2006.01) |
| *A61M 5/145* | (2006.01) |

(52) U.S. Cl.
CPC ............. *A61M 5/007* (2013.01); *A61B 5/055* (2013.01); *A61B 5/7475* (2013.01); *A61B 6/032* (2013.01); *A61B 6/035* (2013.01); *A61B 6/037* (2013.01); *A61B 6/4447* (2013.01); *A61B 6/467* (2013.01); *A61B 6/481* (2013.01); *A61B 8/00* (2013.01); *A61B 8/481* (2013.01); *A61B 90/50* (2016.02); *A61B 2560/0487* (2013.01); *A61M 5/14546* (2013.01); *G01R 33/5601* (2013.01)

(58) Field of Classification Search
CPC ....... A61B 5/055; A61B 5/7475; A61B 6/032; A61B 6/035; A61B 6/037; A61B 6/4447; A61B 6/467; A61B 6/481; A61B 8/00; A61B 8/481; A61B 90/50; A61B 2560/0487; A61M 5/007; A61M 5/14546; G01R 33/5601
USPC ......................................... 600/431
See application file for complete search history.

(56) References Cited

U.S. PATENT DOCUMENTS

| | | | |
|---|---|---|---|
| 6,031,888 A * | 2/2000 | Ivan ..................... | A61B 6/4441 378/196 |
| 2014/0088494 A1 * | 3/2014 | Shearer, Jr. ............. | A61M 5/00 604/67 |

* cited by examiner

*Primary Examiner* — Michael J Carey
(74) *Attorney, Agent, or Firm* — Harness, Dickey & Pierce, P.L.C.

(57) ABSTRACT

A system is for contrast agent-based medical imaging. In an embodiment, the system includes a gantry of a medical imaging device; a contrast agent injection device; and a support arm including a frame element, a first connecting element and a second connecting element. In an embodiment, the frame element is connected to a stationary support frame of the gantry via the first connecting element such that at least part of the frame element is mounted to be movable relative to the stationary support frame of the gantry, and the contrast agent injection device is connected to at least part of the frame element via the second connecting element such that the contrast agent injection device is mounted to be movable relative to at least part of the frame element.

30 Claims, 5 Drawing Sheets

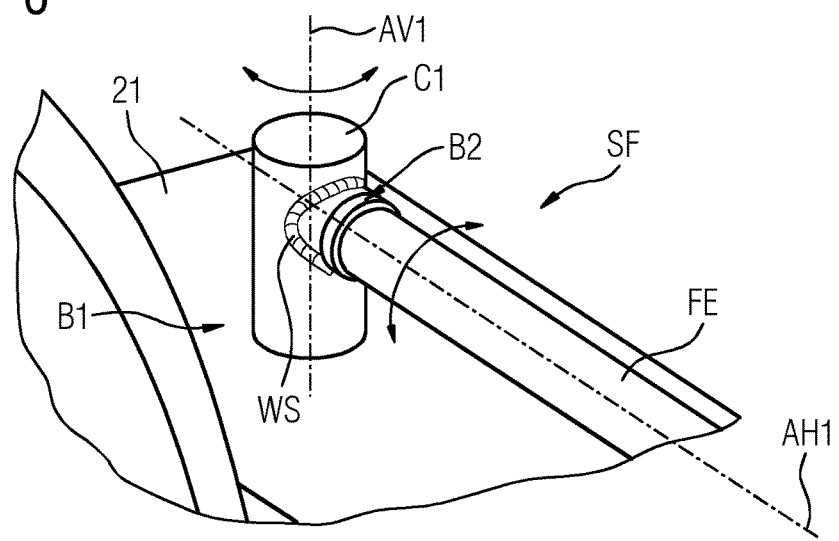
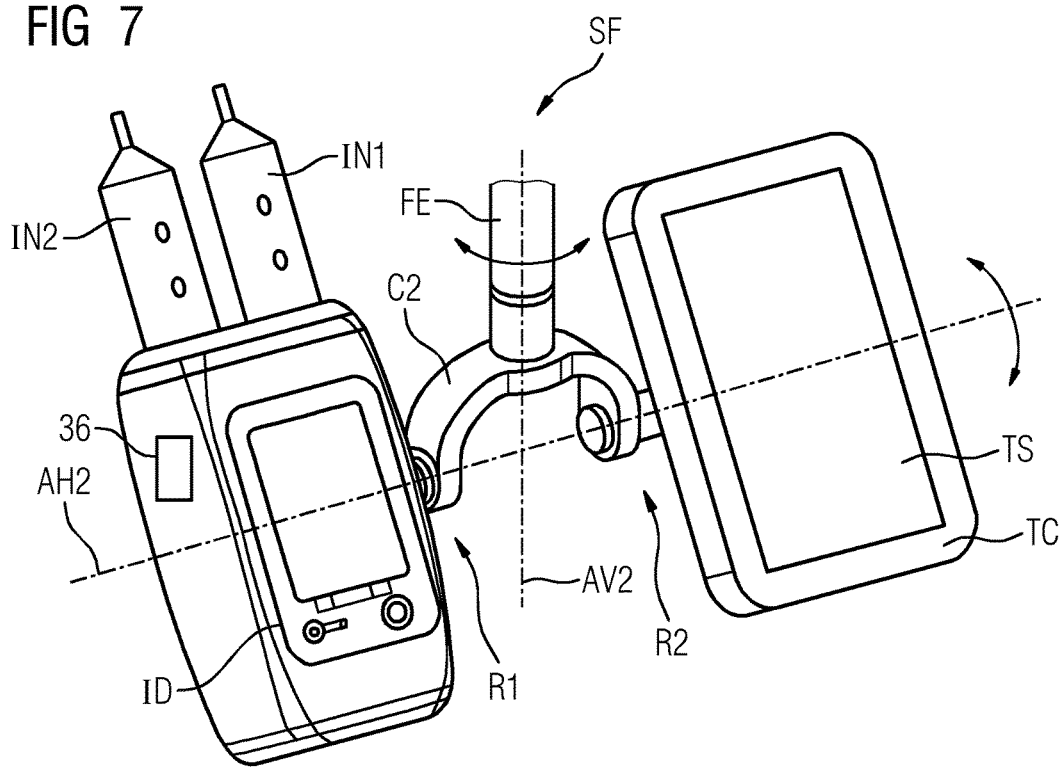

SYSTEM FOR CONTRAST AGENT-BASED MEDICAL IMAGING

PRIORITY STATEMENT

The present application hereby claims priority under 35 U.S.C. § 119 to German patent application number DE 202016004185.2 filed Jun. 30, 2016, the entire contents of which are hereby incorporated herein by reference.

FIELD

At least one embodiment of the invention generally relates to a system for contrast agent-based medical imaging. Embodiments of a method for operating a system for contrast agent-based medical imaging, a computer program product and a computer-readable medium are also disclosed.

BACKGROUND

Contrast agent-based imaging can occur, for example, within the framework of an examination by way of computed tomography (CT), magnetic resonance tomography (MR), ultrasound (US), molecular imaging (MI) or single-photon emission computed tomography (SPECT). It is important in this connection firstly to synchronize imaging and injection in relation to the chronological sequence and secondly, to choose the correct parameterization at the medical imaging device and at the contrast agent injection device in each case.

Depending on the imaging modality, these steps can be performed so as to be distributed among different user interfaces. The user interfaces can be located in different rooms, for example in the examination room and/or in the control room. The medical imaging device and/or the contrast agent injection device is/are located in the examination room. The contrast agent injection device is often arranged on a trolley which can be moved on wheels, or is arranged on a support arm which is suspended from the ceiling.

An imaging console for operating the medical imaging device and/or a contrast agent injection console for operating the contrast agent injection device is typically permanently installed in the control room. Operating elements for operating the contrast agent injection device can be arranged, for example, in the form of hardware on the contrast agent injection device and/or be output via a touch-sensitive screen arranged on the contrast agent injection device. Operating elements for operating the medical imaging device can be arranged, for example, in the form of hardware on the medical imaging device and/or be output via a touch-sensitive screen arranged on the medical imaging device.

SUMMARY

At least one embodiment of the invention enables improved operation of a system for contrast agent-based medical imaging.

Embodiments of the invention are considered in the claims.

Unless stated otherwise, the term "method" stands for the method for operating a system for contrast agent-based medical imaging below. Unless stated otherwise, the term "system" stands for the system for contrast agent-based medical imaging below.

The inventive system of at least one embodiment for contrast agent-based medical imaging includes:

a gantry of a medical imaging device,
a contrast agent injection device,
a support arm having a frame element, a first connecting element and a second connecting element,
wherein the frame element is connected to a stationary support frame of the gantry by way of the first connecting element in such a way that at least part of the frame element is mounted so it can be moved relative to the stationary support frame of the gantry,
wherein the contrast agent injection device is connected to the at least part of the frame element by way of the second connecting element in such a way that the contrast agent injection device is mounted so it can be moved relative to at least part of the frame element.

The method of at least one embodiment disclosed hereby for operating a system for contrast agent-based medical imaging, having a medical imaging device and a contrast agent injection device, comprises:

outputting a first operating element for operating the medical imaging device via a touch-sensitive screen,
inputting a first item of information for operating the medical imaging device via the touch-sensitive screen using the first operating element,
outputting a second operating element for operating the contrast agent injection device via the touch-sensitive screen,
inputting a second item of information for operating the contrast agent injection device via the touch-sensitive screen using the second operating element.

One embodiment of the invention provides that the system for contrast agent-based medical imaging also has at least the following components:

a medical imaging device,
a contrast agent injection device,
a touch-sensitive screen,
a data processing unit, wherein the data processing unit and/or the system is/are designed to carry out a method according to any one of the embodiments which is disclosed in the description and/or in the claims.

One embodiment of the invention provides that the system also has a tablet computer, wherein the tablet computer has the touch-sensitive screen and/or the data processing unit.

The computer program product disclosed hereby has a computer program which can be loaded into a storage device of a data processing unit, having program segments in order to carry out all steps of the method according to one of the embodiments, which are disclosed in the description and/or in the claims, when the computer program is executed by the data processing unit.

Program segments which can be read and executed by a data processing unit are stored on the computer-readable medium disclosed hereby in order to carry out all steps of the method according to one of the embodiments, which are disclosed in the description and/or in the claims, when the program segments are executed by the data processing unit.

BRIEF DESCRIPTION OF THE DRAWINGS

Some embodiments will be illustrated below with reference to the accompanying figures. The representation in the figures is schematic, highly simplified and not necessarily to scale.

In the drawings:

FIG. 6 to FIG. 9 show different partial views of the system for contrast agent-based medical imaging.

DETAILED DESCRIPTION OF THE EXAMPLE EMBODIMENTS

Figure 1:
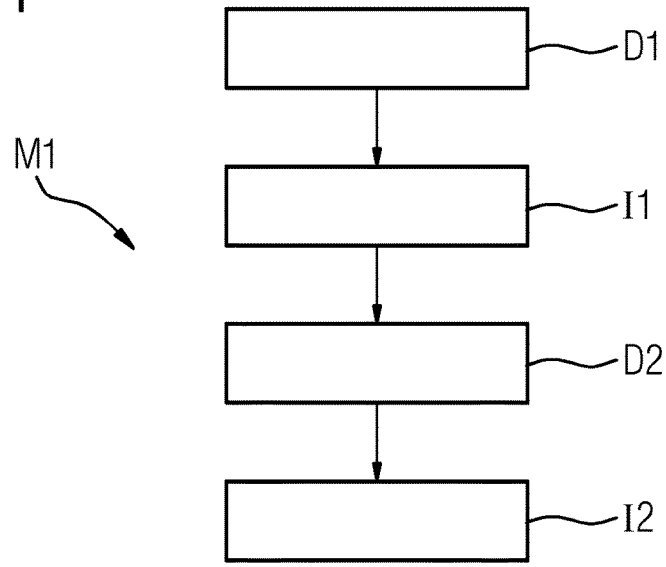
FIG. 1 shows a flowchart for a method for operating a system for contrast agent-based medical imaging.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The inventive system of at least one embodiment for contrast agent-based medical imaging includes:
  a gantry of a medical imaging device,
  a contrast agent injection device,
  a support arm having a frame element, a first connecting element and a second connecting element,
  wherein the frame element is connected to a stationary support frame of the gantry by way of the first connecting element in such a way that at least part of the frame element is mounted so it can be moved relative to the stationary support frame of the gantry,
  wherein the contrast agent injection device is connected to the at least part of the frame element by way of the second connecting element in such a way that the contrast agent injection device is mounted so it can be moved relative to at least part of the frame element.

One embodiment of the invention provides
  that the second connecting element has a first connecting region in which the contrast agent injection device can be connected to the second connecting element, and/or
  that the second connecting element has a second connecting region in which an additional component can be connected to the second connecting element, whereas the contrast agent injection device is connected to the second connecting element in the first connecting region.

One embodiment of the invention provides
  that the frame element is connected to the stationary support frame of the gantry by way of the first connecting element in such a way that the frame element is mounted so it can be rotated about a first axis of rotation relative to the stationary support frame of the gantry and/or is mounted so it can be tilted about a first tilt axis,
  that the contrast agent injection device is connected to the frame element by way of the second connecting element in such a way that the contrast agent injection device is mounted so it can be rotated about a second axis of rotation relative to the frame element and/or can be tilted about a second tilt axis, and/or
  that the additional component is connected to the frame element by way of the second connecting element in such a way that the additional component can be mounted so it can be rotated about the second axis of rotation relative to the frame element and/or can be tilted about the second tilt axis and/or about a third tilt axis.

One embodiment of the invention provides,
  that the contrast agent injection device can be positively and/or detachably connected to the second connecting element and/or
  that the additional component can be positively and/or detachably connected to the second connecting element.

One embodiment of the invention provides that the first connecting region and second connecting region are arranged symmetrically in relation to the second axis of rotation.

One embodiment of the invention provides that the additional component has a touch-sensitive screen and/or a tablet computer.

One embodiment of the invention provides that the support frame has a cavity which extends along the support frame in such a way that a cable can be arranged in the cavity, and this extends inside the cavity from the first connecting element to the second connecting element.

One embodiment of the invention provides that the system also has a cable which extends inside the cavity from an interior of the stationary support frame of the gantry to the contrast agent injection device and/or to the additional component.

One embodiment of the invention provides,
that the first connecting element has a first mounting region, wherein the frame element is mounted by way of the first mounting region so it can be rotated about a first axis of rotation relative to the stationary support frame of the gantry, and/or
that the first connecting element has a second mounting region, wherein the frame element can be mounted by way of the second mounting region so it can be tilted about a first tilt axis relative to the stationary support frame of the gantry.

One embodiment of the invention provides
that the first connecting element in the first mounting region has a rotation-limiting mechanism for limiting the rotation of the frame element about the first axis of rotation to a specific rotation angle range and/or
that the first connecting element in the second mounting region has a tilting movement-limiting mechanism for limiting the tilting movement of the frame element about the first tilt axis to a specific tilt angle range.

One embodiment of the invention provides
that the rotation-limiting mechanism has a channel in the form of an arc and a pin guided in the channel,
that the rotation of the frame element about the first axis of rotation is coupled to a movement of the pin along the channel and is limited to a rotation angle range encompassed by the channel.

One embodiment of the invention provides
that the first connecting element in the first mounting region has a rotation angle-stabilizing mechanism for stabilizing a rotation angle of the frame element in relation to a rotation of the frame element about the first axis of rotation and/or
that the first connecting element in the second mounting region has a tilt angle-stabilizing mechanism for stabilizing a tilt angle of the frame element in relation to a tilting movement of the frame element about the first tilt axis.

One embodiment of the invention provides
that the rotation angle-stabilizing mechanism has at least one friction contact,
that the rotation of the frame element about the first axis of rotation is coupled to friction at the at least one friction contact of the rotation angle-stabilizing mechanism,
that the rotation angle can be stabilized by way of the static friction at the at least one friction contact of the rotation angle-stabilizing mechanism.

One embodiment of the invention provides
that the tilt angle-stabilizing mechanism has at least one friction contact,
that the tilting movement of the frame element about the first tilt axis is coupled to friction at the at least one friction contact of the tilt angle-stabilizing mechanism,
that the tilt angle can be stabilized by way of the static friction at the at least one friction contact of the tilt angle-stabilizing mechanism.

One embodiment of the invention provides
at least one friction partner of the at least one friction contact of the rotation angle-stabilizing mechanism is arranged annularly and/or in the manner of an arc about the first axis of rotation and/or is produced from plastics material and/or
that at least one friction partner of the at least one friction contact of the tilt angle-stabilizing mechanism is arranged annularly and/or in the manner of an arc about the first tilt axis and/or is produced from plastics material.

One embodiment of the invention provides
that the rotation angle-stabilizing mechanism has a tensioning element which cooperates with the at least one friction contact of the rotation angle-stabilizing mechanism in such a way that the contact pressure underlying the friction at the at least one friction contact of the rotation angle-stabilizing mechanism is caused at least partly by a mechanical tensioning of the tensioning element of the rotation angle-stabilizing mechanism, and/or
that the tilt angle-stabilizing mechanism has a tensioning element which cooperates with the at least one friction contact of the tilt angle-stabilizing mechanism in such a way that the contact pressure underlying the friction at the at least one friction contact of the tilt angle-stabilizing mechanism is caused at least partly by a mechanical tensioning of the tensioning element of the tilt angle-stabilizing mechanism.

One embodiment of the invention provides
that the tensioning element of the rotation angle-stabilizing mechanism has a spring and/or wherein the spring of the tensioning element of the rotation angle-stabilizing mechanism has one or more winding(s) which are arranged around the first axis of rotation, and/or
that the tensioning element of the tilt angle-stabilizing mechanism has a spring and/or wherein the spring of the tensioning element of the tilt angle-stabilizing mechanism has one or more winding(s) which are arranged around the first tilt axis.

One embodiment of the invention provides
that the first axis of rotation is vertical and/or the first tilt axis is horizontal.

One embodiment of the invention provides
that the second axis of rotation is vertical and/or the second tilt axis is horizontal at least for a tilt angle of the frame element in relation to a tilting movement of the frame element about the first tilt axis.

The use of the support arm according to one of the embodiments, which are disclosed in the description and/or in the claims, makes it possible to dispense with an arrangement of the support arm on the ceiling of the examination room and with an arrangement of the support arm on the floor of the examination room. The space requirements and the requirements on the constructional conditions of the examination room are reduced thereby. In particular, the frame element can be arranged between the first connecting element and the second connecting element.

The tiltable mounting about the first tilt axis and/or the second tilt axis makes it possible to adjust the height of the contrast agent injection device, for example, as a function of the needs of the user and/or the requirements of the examination. The user can, for example, drive the tilting movement manually himself and thereby bring the support arm into the desired position.

In particular, as an alternative to the additional component being mounted so it can tilt about the second tilt axis, the additional component can be mounted about a third tilt axis. In particular, the third tilt axis can be parallel to the second tilt axis. In particular, the spacing between the second tilt axis and the third tilt axis can be less than, for example, a diagonal of the touch-sensitive screen or, for example, a fifth of the diagonal of the touch-sensitive screen.

In particular the second connecting element in the first connecting region can be designed for positive and/or detachable coupling and decoupling of the contrast agent injection device. In particular, the second connecting element in the second connecting region can be designed for positive and/or detachable coupling and decoupling of the additional component. The contrast agent injection device and/or the additional component can, for example, be manually coupled or decoupled by the user.

The additional component can alternatively or additionally have one or more intervention tools. In particular, the additional component can be a tablet computer according to one of the embodiments which is disclosed in the description and/or claims. In particular, the tablet computer can be designed for operation of the medical imaging device and/or for operation of the contrast agent injection device.

One embodiment of the invention provides that a normal vector of a screen surface of the touch-sensitive screen is essentially perpendicular to the second tilt axis. One embodiment of the invention provides that the contrast agent injection device has a flat input and/or display region and that a normal vector of the flat input and/or display region of the contrast agent injection device is essentially perpendicular to the second tilt axis. The flat input and/or display region of the contrast agent injection device can be integrated, for example, in a covering of the contrast agent injection device. One embodiment of the invention provides that the normal vector of the screen surface of the touch-sensitive screen, which is directed away from the touch-sensitive screen, is essentially parallel to the normal vector of the flat input and/or display region of the contrast agent injection device, which is directed away from the contrast agent injection device. The contrast agent injection device and the tablet computer can therefore be arranged clearly side by side on the second connecting element. The improved clear arrangement means that sources of errors can be eliminated when operating the medical imaging device and/or contrast agent injection device. In particular, the contrast agent injection device and tablet computer can be provided by way of a rotation of the frame element about the first axis of rotation on the front of the medical imaging device, where the patient-bearing device is located, and on the back of the medical imaging device. Unnecessary distances to be covered by the user can therefore be avoided.

The frame element can be formed, for example, by a steel pipe and/or have a plastics material covering. The support arm, in particular the frame element, can be covered for example with paint. In particular, a color adjustment to the gantry and/or the fulfillment of requirements on the electrostatic safety can be achieved with the aid of the paint.

The cable can have, for example, one or more line(s) for supplying the contrast agent injection device and/or the additional component with power and/or one or more line(s) for data transfer between the medical imaging device on the one hand and the contrast agent injection device and/or additional component on the other hand.

The stationary support frame of the gantry can be designed, for example in the region of the first mounting region, to receive the first connecting element and/or to absorb the forces and/or moments acting on the support arm. For example, a receiving unit, led through the covering of the gantry and/or integrated in the covering of the gantry, can be arranged in the region of the first mounting region in order to receive the first connecting element.

The rotation can be limited to a specific rotation angle range with the aid of the channel and the pins. In particular, a collision of the support arm and/or contrast agent injection device with the patient and/or part of the medical imaging device, for example the gantry, can be avoided thereby.

One embodiment of the invention provides that the second connecting element has a first rotation angle-stabilizing mechanism for stabilizing a rotation angle of the contrast agent injection device in relation to a rotation of the contrast agent injection device about the second axis of rotation and/or that the second connecting element has a first tilt angle-stabilizing mechanism for stabilizing a tilt angle of the contrast agent injection device in relation to a tilting movement of the contrast agent injection device about the second tilt axis. One embodiment of the invention provides that the second connecting element has a second rotation angle-stabilizing mechanism for stabilizing a rotation angle of the additional component in relation to a rotation of the contrast agent injection device about the second axis of rotation and/or that the second connecting element has a second tilt angle-stabilizing mechanism for stabilizing a tilt angle of the additional component in relation to a tilting movement of the additional component about the second tilt axis.

The first rotation angle-stabilizing mechanism of the second connecting element, the second rotation angle-stabilizing mechanism of the second connecting element, the first tilt angle-stabilizing mechanism of the second connecting element and/or the second tilt angle-stabilizing mechanism of the second connecting element can each be developed with at least one friction contact and/or tensioning element, as is described using the example of the rotation angle-stabilizing mechanism of the first connecting element and/or using the example of the tilt angle-stabilizing mechanism of the first connecting element.

In particular, the friction partner of the at least one friction contact of the rotation angle-stabilizing mechanism can be chosen and arranged such that the friction at the at least one first friction contact is sufficiently strong on the one hand for the forces and/or moments, which are caused by the mass and/or by the operation of the contrast agent injection device and/or the additional component, to not lead to a rotation of the frame element about the first axis of rotation and, on the other hand, a rotation of the frame element about the first axis of rotation can be manually driven by a user by applying muscle strength to the support arm.

In particular, the friction partner of the at least one friction contact of the tilt angle-stabilizing mechanism can be chosen and arranged such that the friction at the friction contact of the tilt angle-stabilizing mechanism is sufficiently strong on the one hand for the forces and/or moments, which are caused by the mass and/or by the operation of the contrast agent injection device and/or additional component, to not lead to a tilting movement of the frame element about the first tilt axis and, on the other hand, a tilting movement of the frame element about the first tilt axis can be manually driven by a user by applying muscle strength to the support arm.

In particular, the at least one friction partner of the at least one friction contact of the rotation angle-stabilizing mechanism can have a region which is produced from plastics material and/or a plastics material surface. In particular, the at least one friction partner of the at least one friction contact of the tilt angle-stabilizing mechanism can have a region which is produced from plastics material and/or has a plastics material surface. The plastics material can, for example, be produced from polyamide (PA) and/or be based on polyamide (PA).

The method of at least one embodiment disclosed hereby for operating a system for contrast agent-based medical imaging, having a medical imaging device and a contrast agent injection device, comprises:
  outputting a first operating element for operating the medical imaging device via a touch-sensitive screen,
  inputting a first item of information for operating the medical imaging device via the touch-sensitive screen using the first operating element,
  outputting a second operating element for operating the contrast agent injection device via the touch-sensitive screen,
  inputting a second item of information for operating the contrast agent injection device via the touch-sensitive screen using the second operating element.

In one particular embodiment, it can be provided that the method also comprises one or more of the following step(s):
  outputting a third operating element via the touch-sensitive screen, wherein the third operating element comprises a third item of information which relates to a medical examination via the medical imaging device and/or a contrast agent dose by way of the contrast agent injection device,
  inputting the first item of information by way of a first input command using the first operating element and the third operating element.

In an embodiment it can be provided that the third item of information is ascertained on the basis of the second item of information.

In an embodiment it can be provided that the method also comprises one or more of the following steps:
  outputting a fourth operating element via the touch-sensitive screen, wherein the fourth operating element comprises a fourth item of information which relates to a medical examination by way of the medical imaging device and/or a contrast agent dose by way of the contrast agent injection device,
  inputting the second item of information by way of a second input command using the second operating element and the fourth operating element.

In an embodiment it can be provided that the fourth item of information is ascertained on the basis of the first item of information.

In an embodiment it can be provided that the method also comprises the following step:
  executing a software application for operating the medical imaging device and the contrast agent injection device which comprises the first operating element and the second operating element.

In an embodiment it can be provided that the method also comprises one or more of the following step(s):
  executing a first software application for operating the medical imaging device which comprises the first operating element and/or the fourth operating element,
  executing a second software application for operating the contrast agent injection device which comprises the second operating element and/or the third operating element.

In an embodiment it can be provided that the method also comprises the following step:
  providing an interface for transferring information between the first software application and the second software application.

In an embodiment it can be provided that the interface is based on the client-server model.

In an embodiment it can be provided
  that the interface comprises a memory area,
  that the first software application can read and/or write access the memory area,
  that the second software application can read and/or write access the memory area.

In an embodiment it can be provided that the software application is executed by a data processing unit.

In an embodiment it can be provided that the first software application and/or the second software application is/are executed by a data processing unit.

In an embodiment it can be provided that the method also comprises the following step:
  transferring data between the data processing unit and the medical imaging device, wherein the data comprises the first item of information and/or the fourth item of information.

In an embodiment it can be provided that the method also comprises the following step:
  transferring data between the data processing unit and the contrast agent injection device, wherein the data comprises the second item of information and/or the third item of information.

In an embodiment it can be provided that a tablet computer has the touch-sensitive screen and/or the data processing unit.

One embodiment of the invention provides that the system for contrast agent-based medical imaging also has st least the following components:
  a medical imaging device,
  a contrast agent injection device,
  a touch-sensitive screen,
  a data processing unit, wherein the data processing unit and/or the system is/are designed to carry out a method according to any one of the embodiments which is disclosed in the description and/or in the claims.

In an embodiment, the data processing unit can be designed as part of a data processing system, for example a computer network, a computer, a tablet computer, a smartphone or the like. This data processing system can be provided, for example, by a third-party provider who is distinguished in particular from the manufacturer of the contrast agent injection device and/or the manufacturer of the medical imaging device.

One embodiment of the invention provides that the system also has a tablet computer, wherein the tablet computer has the touch-sensitive screen and/or the data processing unit.

The computer program product disclosed hereby has a computer program which can be loaded into a storage device of a data processing unit, having program segments in order to carry out all steps of the method according to one of the embodiments, which are disclosed in the description and/or in the claims, when the computer program is executed by the data processing unit.

Program segments which can be read and executed by a data processing unit are stored on the computer-readable medium disclosed hereby in order to carry out all steps of the method according to one of the embodiments, which are disclosed in the description and/or in the claims, when the program segments are executed by the data processing unit.

Operation of the medical imaging device can comprise, for example, choosing and/or modifying examination parameters. Operation of the medical imaging device can comprise, for example, movement of the bearing plate of the patient-bearing device relative to the gantry of the medical imaging device. Operation of the medical imaging device can comprise, for example, setting an operating mode of the medical imaging device. Setting an operating mode of the medical imaging device can comprise, for example, starting and/or ending the examination by way of the medical imaging device and/or starting and/or ending the acquisition of imaging raw data by way of the imaging data acquisition device.

Information for operating the medical imaging device can comprise, for example, one or more examination parameter(s) and/or a modification of one or more examination parameter(s). Information for operating the medical imaging device can comprise, for example, a position and/or a change in the position of the bearing plate relative to the gantry and/or relative to the bearing base. Information for operating the medical imaging device can comprise, for example, a command for starting and/or ending the examination by way of the medical imaging device and/or a command for starting and/or ending the acquisition of imaging raw data by way of the imaging data acquisition device.

The examination parameters can relate, for example, to an examination by way of the medical imaging device and/or an examination protocol for an examination by way of the medical imaging device. The examination parameters can relate, for example, to the patient and/or the imaging and/or the contrast agent dose.

The examination parameters, which relate to the patient, can comprise, in particular, anatomical data and/or biographical data of the patient, for example the weight and/or age of the patient. The anatomical data of the patient can comprise, in particular, an anatomy which has been ascertained, for example, on the basis of one or more preceding examination(s). The examination parameters, which relate to imaging, can comprise, in particular, the examination region, for example a position and/or an anatomy of the examination region, and/or a progression over time of the imaging, for example a start time and/or duration of the imaging, and/or data for radiation, for example power and/or a radiation dose. The examination parameters, which relate to the contrast agent dose, can comprise, in particular, a designation and/or a quantity of the contrast agent and/or a progression over time of the contrast agent dose, for example a start time and/or duration of the contrast agent dose.

Operation of the contrast agent injection device can comprise, for example, choosing and/or modifying injection parameters. Operation of the contrast agent injection device can comprise, for example, setting an operating mode of the contrast agent injection device. Setting an operating mode of the contrast agent injection device can comprise, for example, starting and/or ending the contrast agent dose by way of the contrast agent injection device.

Information for operating the contrast agent injection device can comprise, for example, one or more injection parameter(s) and/or a modification or one or more injection parameter(s). Information for operating the contrast agent injection device can comprise, for example, a command for starting and/or ending the contrast agent dose via the contrast agent injection device.

The injection parameters can relate, for example, to a contrast agent dose by way of the contrast agent injection device and/or an injection protocol for a contrast agent dose via the contrast agent injection device. The injection parameters can relate, for example, to the patient and/or imaging and/or the contrast agent dose.

The injection parameters, which relate to the patient, can comprise, in particular, anatomical and/or biographical data of the patient. The injection parameters, which relate to the contrast agent dose, can comprise, in particular, a designation and/or a quantity of the contrast agent and/or a progression over time of the contrast agent dose, for example a start time and/or duration of the contrast agent dose.

Information can be input using an operating element, for example, by inserting the information in the form of a character, in particular text and/or a number, in an input field of the operating element and/or by choosing the information from a plurality of items of information which are displayed in a menu of the operating element.

The contrast agent dose can comprise, for example, an injection of a first contrast agent, an injection of a second contrast agent, an injection of a solution without contrast agent, in particular a saline solution, or the like or combinations thereof.

The first input command and/or the second input command can, in particular, be a gesture, for example a "drag and drop" gesture.

In particular, a patient-specific modification of injection parameters can be ascertained and output in the form of the fourth item of information via the medical imaging device based on anatomical and/or biographical data of the patient, which has been ascertained, for example, in the form of the first item of information.

The software application can, in particular, be a software application installed on the tablet computer, with which the medical imaging device and the contrast agent injection device can be controlled. The data does not then need to be exchanged between the medical imaging device and the contrast agent injection device by way of two different software applications and can proceed by way of a single software application.

In particular, the third item of information can be ascertained by way of the second software application on the basis of the second item of information. In particular, the fourth item of information can be ascertained by way of the first software application on the basis of the first item of information. The first software application and/or the second software application can, in particular, be installed on the tablet computer. The medical imaging device can, for example, be operated fully and/or at least partially with the first software application. The contrast agent injection device can, for example, be operated fully and/or at least partially with the second software application. In particular, it can be provided that the software application is embedded in a graphic user interface and/or that the first software application and/or the second software application is/are embedded in a graphic user interface. The graphic user interface can be provided, for example, by an operating system installed on the tablet computer.

In particular, the interface for transferring information between the first software application and the second software application can be designed in the form of software. Communication, for example, between the first software application, which controls the medical imaging device, and the second software application, which controls the contrast agent injection device, can be established via the interface. In particular it can be provided that information can be transferred bidirectionally via the interface. In particular, injection parameters and examination parameters can thereby be exchanged for documentation purposes between the medical imaging device and the contrast agent injection device.

The first software application can, for example, propose optimized injection parameters on the basis of examination parameters, which are present in the first software application, and pass these on to the second software application.

The second software application can, for example, pass injection parameters, which have actually been used by the contrast agent injection device for the contrast agent dose, from the contrast agent injection device to the first software application. The injection parameters can thereby be archived, for example in the form of DICOM-data, together with imaging data, which has been acquired by the medical imaging device. For example, information can thereby be transferred from the contrast agent injection device to the medical imaging device and/or be documented together with results of imaging.

Examination parameters can also be exchanged between the first software application and the second software application by way of the first input command and/or by way of the second input command. Injection parameters can also be exchanged between the first software application and the second software application by way of the first input command and/or by way of the second input command.

A data file with the information to be transferred can be stored in the memory area of the interface, for example, by the first software application and/or by the second software application, and be read by the first software application and/or by the second software application. The format of the data file can, for example, be universally chosen such that information can also be transferred in this way between a first software application and a second software application which have been provided by different manufacturers.

The tablet computer can have, for example, a data transfer module which is designed for transferring data between the tablet computer and the medical imaging device and/or for transferring data between the tablet computer and the contrast agent injection device.

In particular, the tablet computer can establish a data link with the medical imaging device for transferring the data between the data processing unit and the medical imaging device. In particular, the tablet computer can establish a data link with the contrast agent injection device for transferring the data between the data processing unit and the contrast agent injection device. The data link can be, for example, wireless, in particular on the basis of WLAN, Bluetooth or NFC, and/or be wired.

The use of a tablet computer, on which the first software application and the second software application are installed, in the examination room makes it possible to dispense with the installation of software for operating the contrast agent injection device on the imaging console in the control room. Software for operating the contrast agent injection device, which is supplied by third-party providers and cannot or must not be installed on the imaging console, can often be easily installed on the tablet computer. The use of third-party provider software for operating the contrast agent injection device is simplified thereby.

The use of a tablet computer, on which the first software application and the second software application are installed, in the examination room, makes it possible to dispense with a contrast agent injection console in the control room. The costs for the contrast agent injection device as well as the expenditure for the installation of the contrast agent injection device are reduced thereby.

The medical imaging device and the contrast agent injection device can be directly connected to each other by way of a data link. For synchronization of injection and imaging time-critical and/or safety-relevant communication, for example, can take place between the medical imaging device and the contrast agent injection device by way of this direct data link. This direct data link can be, for example wired and/or based on a TTL signal.

Alternatively and/or additionally this direct data link can have a bus system which is based, for example, on CANopen, TCP/IP or the like. In particular when an exchange of injection parameters between the medical imaging device and the contrast agent injection device is set up by way of the direct data link and/or by way of the interface, the contrast agent injection device can be parameterized and/or controlled by way of the medical imaging device and thereby be adapted to the needs of the user, to the requirements of the examination and/or the individual features of the patient.

In particular it can be provided that the data processing unit is formed at least partially by a data processing system and/or that one or more components of the data processing unit are formed at least partially by a data processing system.

The data processing system can have, for example, one or more components in the form of hardware and/or one or more components in the form of software. The data processing system can be formed, for example, at least partially by a cloud computing system. The data processing system can be and/or have, for example, a cloud computing system, computer network, computer, tablet computer, smartphone or the like or combinations thereof. The hardware can cooperate, for example, with software and/or be configured by way of software. The software can be executed, for example, by way of the hardware. The hardware can be, for example, a storage system, an FPGA system (field-programmable gate array), an ASIC system (application-specific integrated circuit), a microcontroller system, a processor system and combinations thereof. The processor system can have, for example, a microprocessor and/or a plurality of cooperating microprocessors.

Data can be transferred between components of the data processing system, for example, by way of a suitable data transfer interface in each case. The data transfer interface for data transfer to and/or from a component of the data processing system can be implemented at least partially in the form of software and/or at least partially in the form of hardware. The data transfer interface can be designed, for example, for storing data in and/or for loading data from a sector of the storage system, it being possible to access one or more component(s) of the data processing system on this sector of the storage system.

The computer program can, for example, be loaded in the storage system of the data processing system and be retrieved by the processor system of the data processing system. The data processing system can be formed, for example, by way of the computer program such that the data processing system can carry out the steps of a method according to one of the embodiments, which are disclosed in the description and/or in the claims, when the computer program is executed by the data processing system.

The computer program product can be, for example, the computer program or comprise at least one additional component apart from the computer program. The at least one additional component of the computer program product can be formed as hardware and/or as software. The computer program product can be, for example, a storage medium, on which at least some of the computer program product is stored, and/or have a key for authenticating a user of the computer program product, in particular in the form of a dongle. The computer program product and/or the computer program can have, for example, a cloud application program which is designed for distributing program segments of the computer program among different processing units, in particular different computers, of a cloud computing system, with each of the processing units being designed to execute one or more program segment(s) of the computer program.

For example, the computer program product according to one of the embodiments, which are disclosed in the description and/or in the claims, and/or the computer program according to one of the embodiments, which are disclosed in the description and/or in the claims, can be stored on the computer-readable medium. The computer-readable medium can be, for example, a memory stick, hard disk or another data carrier which can, in particular, be detachably connected to the data processing system or be permanently integrated in the data processing system. The computer-readable medium can form, for example, at least one sector of the storage system of the data processing system.

The medical imaging device can be chosen, for example, from the imaging modalities group comprising an X-ray device, a C-arm X-ray device, a computer tomograph (CT device), a molecular imaging device (MI device), a single-photon emission computed tomograph (SPECT device), a positron emission tomograph (PET device), a magnetic resonance tomograph (MRT device) and combinations thereof (in particular PET-CT device, PET-MR device). The medical imaging device can also have a combination of an imaging modality, which is chosen, for example, from the imaging modalities group, and an irradiation modality. The irradiation modality can have, for example, an irradiation unit for therapeutic irradiation. Without limiting the general inventive idea, a computer tomograph is cited as an example of a medical imaging device in some of the embodiments.

Within the scope of the invention features, which are described in relation to different embodiments and/or different categories (method, device, system, etc.), can be combined to form further embodiments of the invention. In particular, the concrete claims can also be developed with the features which are described or claimed in conjunction with a method. A functional feature of a method can be implemented by way of an appropriately designed concrete component. In addition to the embodiments of the invention explicitly described in this application, a wide variety of further embodiments of the invention are conceivable at which a person skilled in the art can arrive, without departing from the scope of the invention, if it is specified by the claims.

Use of the indefinite article "a" or "an" does not preclude the affected feature from also being present multiple times. Use of the expression "have" does not preclude the terms linked by way of the expression "have" from being identical. For example, the medical imaging device has the medical imaging device. Use of the expression "unit" does not preclude the item to which the expression "unit" refers from having components which are spatially separated from each other.

Use of ordinal number words (first, second, third etc.) in the list of features is primarily used within the context of the present application for the purpose of better distinguishability of the features designated using ordinal number words. The absence of a feature, which is designated by a combination of a given ordinal number word and a term, does not preclude a feature from being present which is designated by a combination of an ordinal number word, which follows the given ordinal number word, and the term.

The expression "on the basis of" can be understood within the context of the present application in particular within the meaning of the expression "using". In particular, wording according to which a first feature is generated (alternatively: ascertained, determined, etc.) on the basis of a second feature, does not preclude the first feature from being generated (alternatively: ascertained, determined, etc.) on the basis of a third feature.

FIG. 1 shows a flowchart for a method for operating a system 1 for contrast agent-based medical imaging, having a medical imaging device 2 and a contrast agent injection device ID.

The method shown in FIG. 1 comprises the following steps:
   outputting D1 a first operating element E1 for operating the medical imaging device 2 via a touch-sensitive screen TS,
   inputting I1 a first item of information for operating the medical imaging device 2 via the touch-sensitive screen TS using the first operating element E1,
   outputting D2 a second operating element E2 for operating the contrast agent injection device ID via the touch-sensitive screen TS,
   inputting I2 a second item of information for operating the contrast agent injection device ID via the touch-sensitive screen TS using the second operating element E2.

Figure 2:
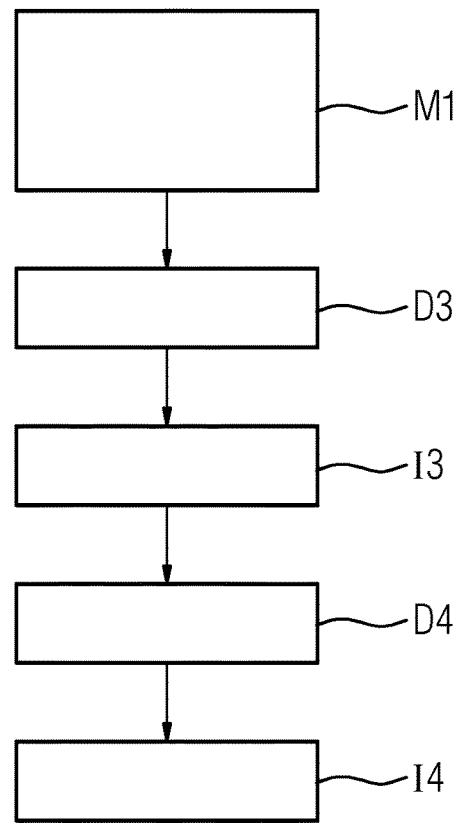
FIG. 2 shows a further flowchart for a method for operating a system for contrast agent-based medical imaging.

FIG. 2 shows a further flowchart for a method for operating a system 1 for contrast agent-based medical imaging, having a medical imaging device 2 and a contrast agent injection device ID.

In addition to the steps shown in FIG. 1, which are illustrated in a simplified manner in FIG. 2 by the group M1 of steps, the method shown in FIG. 2 also comprises the following steps:
   outputting D3 a third operating element E3 via the touch-sensitive screen TS, wherein the third operating element E3 comprises a third item of information which relates to a medical examination by way of the medical imaging device 2 and/or a contrast agent dose by way of the contrast agent injection device ID,
   inputting I3 the first item of information by way of a first input command G1 using the first operating element E1 and the third operating element E3,
   outputting D4 a fourth operating element E4 via the touch-sensitive screen TS, wherein the fourth operating element E4 comprises a fourth item of information which relates to a medical examination by way of the medical imaging device 2 and/or a contrast agent dose by way of the contrast agent injection device ID,
   inputting I4 the second item of information by way of a second input command G2 using the second operating element E2 and the fourth operating element E4.

Figure 3:
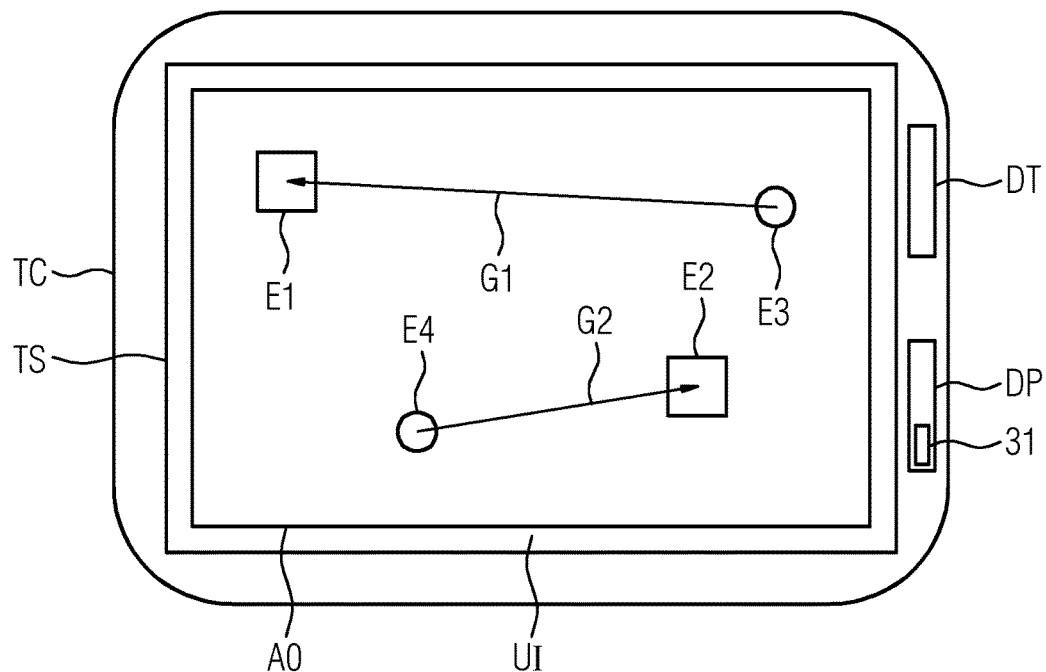
FIG. 3 shows a tablet computer having a software application.

FIG. 3 shows a tablet computer TC having a software application A0 for operating the medical imaging device 2 and the contrast agent injection device ID.

The embodiment shown in FIG. 3 provides
   that the tablet computer TC has the touch-sensitive screen TS, data processing unit DP and data transfer module and
   that the software application A0, which is executed by the data processing unit DP, is installed on the tablet computer TC. The data processing unit DP has the storage device 31 in the form of a computer-readable medium. The data transfer module is designed for transferring data between the tablet computer TC and the medical imaging device 2 and for transferring data between the tablet computer TC and the contrast agent injection device ID. An operating system is also installed on the tablet computer TC, and this provides the graphic user interface UI. The software application A0 is embedded in the graphic user interface UI. The software application A0 comprises the first operating element E1, second operating element E2, third operating element E3 and fourth operating element E4.

The first input command G1 is a gesture, comprising the following steps:
  marking the third operating element E3,
  dragging the third operating element E3 to the first operating element E1,
  dropping the third operating element E3 on the first operating element E1.

The second input command G2 is a gesture, comprising the following steps:
  marking the fourth operating element E4,
  dragging the fourth operating element E4 to the second operating element E2,
  dropping the fourth operating element E4 on the second operating element E2.

Gestures of this kind are also known to a person skilled in the art under the term "Drag and Drop" gesture.

Figure 4:
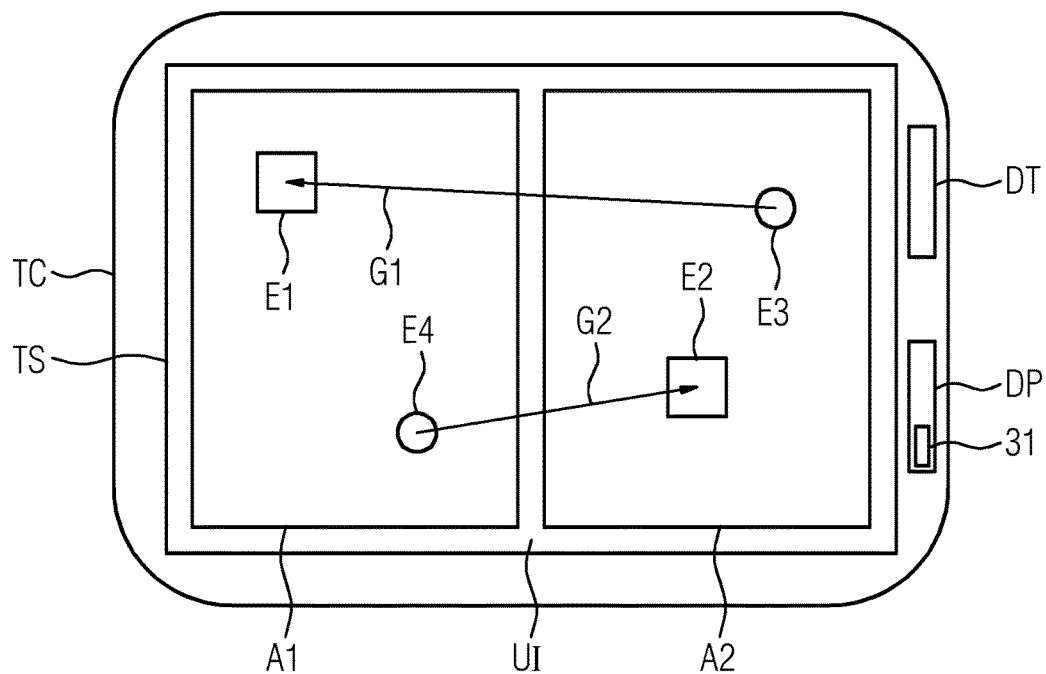
FIG. 4 shows a tablet computer having a first software application and a second software application.

FIG. 4 shows a tablet computer TC having a first software application A1 for operating the medical imaging device 2 and a second software application A2 for operating the contrast agent injection device ID.

The embodiment shown in FIG. 4 provides that the first software application A1 and the second software application A2, which are each executed by the data processing unit DP, are installed on the tablet computer TC. An operating system, which provides the graphic user interface UI, is also provided on the tablet computer TC. The first software application A1 and the second software application A2 are each embedded in the graphic user interface UI. The first software application A1 comprises the first operating element E1 and the fourth operating element E4. The second software application A2 comprises the third operating element E3 and the second operating element E2.

Figure 5:
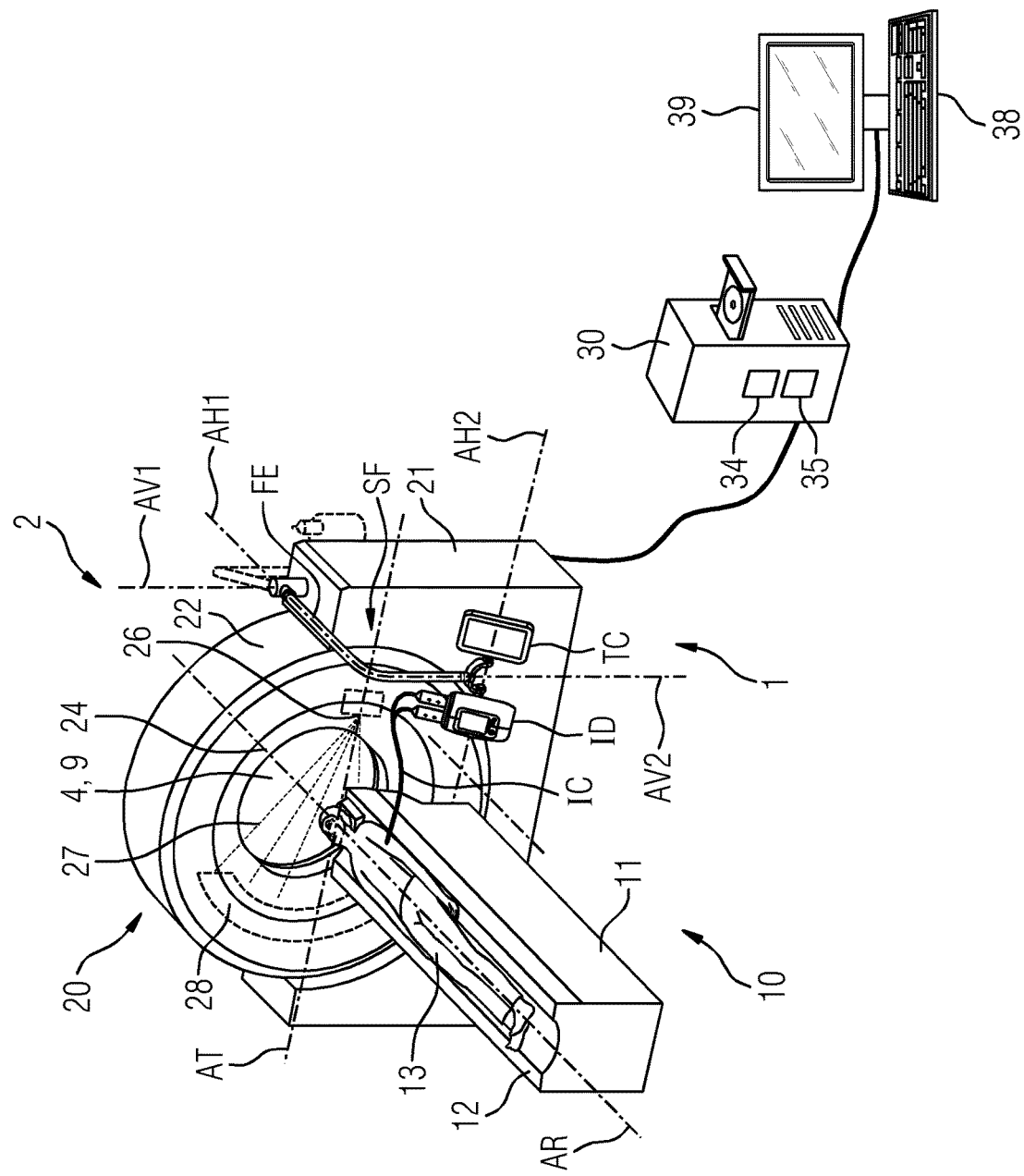
FIG. 5 shows a system for contrast agent-based medical imaging.

FIG. 5 shows a system 1 for contrast agent-based medical imaging, having a medical imaging device 2.

Without limiting the general inventive idea, an exemplary computer tomograph is shown for the medical imaging device 2. The medical imaging device 2 has the gantry 20, the tunnel-like opening 9, the patient-bearing device 10 and the controller 30.

The gantry 20 has the stationary support frame 21, the tilting frame 22 and the rotor 24. The tilting frame 22 is arranged by way of a tilt-bearing device on the stationary support frame 21 so it can tilt about a gantry tilt axis AT relative to the stationary support frame 21. The rotor 24 is arranged by way of a pivot bearing device on the tilting frame 22 so it can pivot about a gantry axis of rotation relative to the tilting frame 22. The gantry tilt axis AT is perpendicular to the system axis AR. The system axis AR and the gantry tilt axis AT are located in a horizontal plane. The gantry axis of rotation is perpendicular to the gantry tilt axis AT and essentially parallel to the system axis AR. The patient 13 can be introduced into the tunnel-like opening 9. The acquisition region 4 is located in the tunnel-like opening 9. A region of the patient 13 that is to be imaged can be positioned in the acquisition region 4 such that the radiation 27 from the radiation source 26 can pass to the region to be imaged and, following an interaction with the region to be imaged, can pass to the radiation detector 28.

The patient-bearing device 10 has the bearing base 11 and the bearing plate 12 for bearing the patient 13. The bearing plate 12 is arranged on the bearing base 11 so it can move relative to the bearing base 11 such that the bearing plate 12 can be introduced in a longitudinal direction of the bearing plate 12, in particular along the system axis AR, into the acquisition region 4.

The medical imaging device 2 is designed for the acquisition of imaging data on the basis of electromagnetic radiation 27. The medical imaging device 2 has an imaging data acquisition unit. The imaging data acquisition unit is a projection data acquisition unit having the radiation source 26, e.g. an X-ray source, and the detector 28, e.g. an X-ray detector, in particular an energy-resolving X-ray detector. The radiation source 26 is arranged on the rotor 24 and designed for emission of radiation 27, e.g. X-ray radiation, with radiation quanta 27. The detector 28 is arranged on the rotor 24 and designed for detection of the radiation quanta 27. The radiation quanta 27 can pass from the radiation source 26 to the region of the patient 13 to be imaged and, following an interaction with the region to be imaged, strike the detector 28. Imaging data of the region to be imaged can be acquired in the form of projection data in this way via the imaging data acquisition unit.

The controller 30 is designed for receiving the imaging data acquired by the imaging data acquisition unit. The controller 30 is designed for controlling the medical imaging device 2. The controller 30 has the image reconstruction device 34. A medical image data set can be reconstructed via the image reconstruction device 34 on the basis of the imaging data.

The medical imaging device 2 has an input device 38 and an output device 39 which are each connected to the controller 30. The input device 38 is designed for inputting control information, e.g. image reconstruction parameters, examination parameters or the like. The output device 39 is designed, in particular, for outputting control information, images and/or sounds.

The embodiment shown in FIG. 5 provides that the system 1 for contrast agent-based medical imaging has the following components:
  a gantry 20 of a medical imaging device,
  a contrast agent injection device ID,
  a support arm SF having a frame element FE, a first connecting element C1 and a second connecting element C2,
  wherein the frame element FE is connected to a stationary support frame 21 of the gantry 20 via the first connecting element C1 in such a way that at least part of the frame element FE is mounted so it can be moved relative to the stationary support frame 21 of the gantry 20,
  wherein the contrast agent injection device ID is connected to at least part of the frame element FE via the second connecting element C2 such that the contrast agent injection device ID is mounted so it can be moved relative to at least part of the frame element FE.

The embodiment shown in FIG. 5 also provides
  that the second connecting element C2 has a first connecting region R1 in which the contrast agent injection device ID can be connected to the second connecting element C2,
  that the second connecting element C2 has a second connecting region R2 in which an additional component can be connected to the second connecting element C2, while the contrast agent injection device ID is connected to the second connecting element C2 in the first connecting region R1, that the frame element FE is connected to the stationary support frame 21 of the gantry 20 via the first connecting element C1 such that the frame element FE is mounted so it can be rotated about a first axis of rotation AV1 relative to the stationary support frame 21 of the gantry 20 and is mounted so it can be tilted about a first tilt axis AH1, that the contrast agent injection device ID is connected to the frame element FE via the second connecting element C2 such that the contrast agent injection device ID is mounted so it can be rotated about a second axis of rotation AV2 relative to the frame element FE and so it can be tilted about a second tilt axis AH2, that the additional component is connected to the frame element FE via the second connecting element C2 such that the additional component is mounted so it can be rotated about the second axis of rotation AV2 relative to the frame element FE about the second tilt axis AH2 and so it can be tilted, and that the additional component is a tablet computer TC.

The embodiment shown in FIG. 5 also provides that the first axis of rotation AV1 is vertical and that the first tilt axis AH1 is horizontal. The second axis of rotation AV2 is vertical and the second tilt axis AH2 is horizontal at least for the tilt angle of the frame element FE shown in FIG. 5 in relation to a tilting movement of the frame element FE about the first tilt axis AH1.

The first connecting element C1 is arranged in a region of a tilting bearing of the tilt bearing device of the gantry 20. The first axis of rotation AV1 runs through the region of the tilting bearing of the tilt bearing device.

In the operating mode of the system 1 shown in FIG. 5 the frame element FE is rotated about the first axis of rotation AV1 such that the second connecting element C2, the contrast agent injection device ID and the tablet computer TC are located at the front of the medical imaging device 2 where the patient-bearing device 10 is also located. A further operating mode of the system 1 is indicated in FIG. 5 by broken lines, in which mode the frame element FE is rotated about the first axis of rotation AV1 such that the second connecting element C2, the contrast agent injection device ID and the tablet computer TC are located at the back of the medical imaging device 2. The gantry 20 of the medical imaging device 2 is located between the front of the medical imaging device 2 and the back of the medical imaging device 2.

The controller 30 has the data transfer unit DT 35. The data transfer unit DT 35 is designed for transferring data between the controller 30 and the tablet computer TC and for transferring data between the controller 30 and the contrast agent injection device ID. The contrast agent injection device ID has the data transfer unit DT 36. The data transfer unit DT 36 is designed for transferring data between the contrast agent injection device ID and the tablet computer TC and for transferring data between the contrast agent injection device ID and the controller 30.

The contrast agent injection device ID is connected to the patient 13 via the injection conduit IC. The contrast agent injection device ID has a first syringe IN1 and a second syringe IN2. A first contrast agent, for example, can be injected into the patient 13 via the first syringe IN1. A second contrast agent and/or a solution without contrast agent, in particular a saline solution, for example, can be injected into the patient 13 with the second syringe IN2.

The embodiment shown in FIG. 6 provides that the first connecting element C1 has a first mounting region B1, wherein the frame element FE is mounted so it can rotate by way of the first mounting region B1 about a first axis of rotation AV1 relative to the stationary support frame 21 of the gantry 20, and that the first connecting element C1 has a second mounting region B2, wherein the frame element FE is mounted so it can tilt by way of the second mounting region B2 about a first tilt axis AH1 relative to the stationary support frame 21 of the gantry 20.

The embodiment shown in FIG. 7 provides that the first connecting region R1 and the second connecting region R2 are arranged symmetrically in relation to the second axis of rotation AV2.

Figure 8:
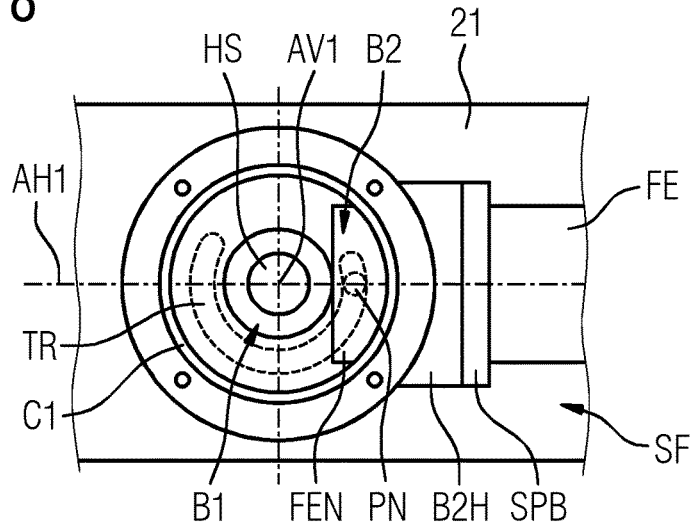

The embodiment shown in FIG. 8 provides that the first connecting element C1 in the first mounting region B1 has a rotation-limiting mechanism and that the rotation-limiting mechanism has a channel TR in the form of an arc and a pin PN guided in the channel TR.

Figure 9:
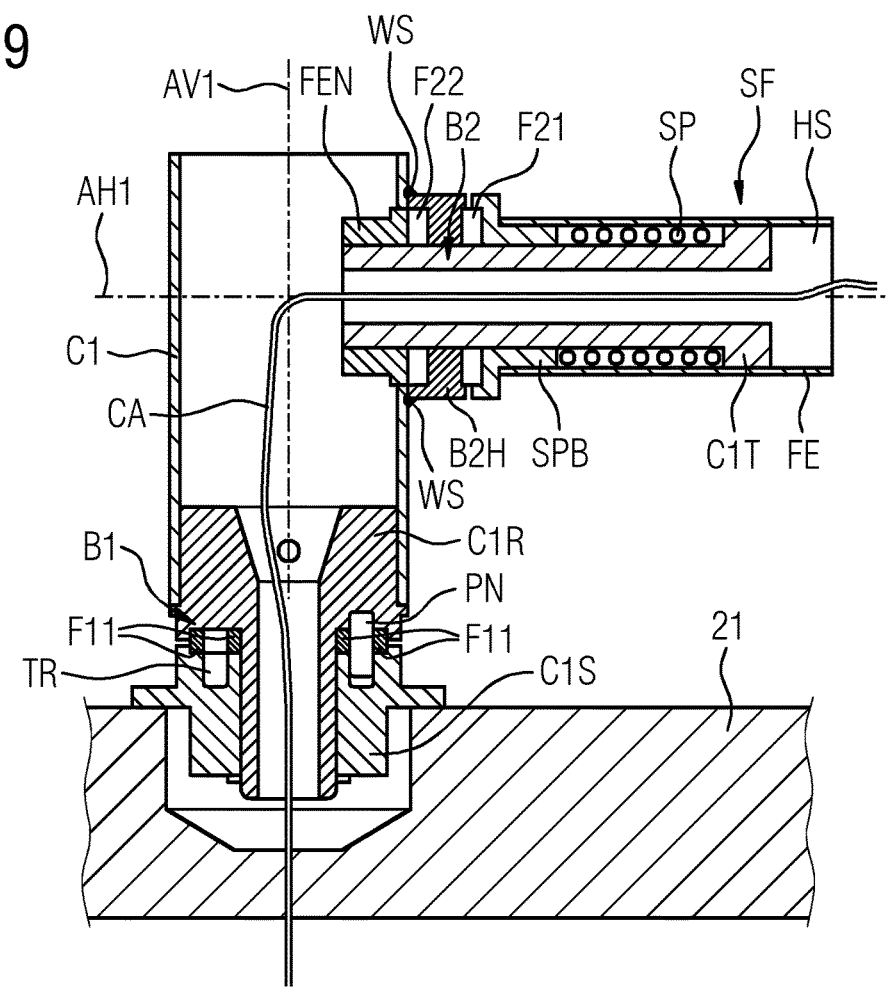

The embodiment shown in FIG. 9 provides that the support frame has a cavity HS, that the system 1 has a cable CA which extends inside the cavity HS from an interior of the stationary support frame 21 of the gantry 20 to the contrast agent injection device ID and to the tablet computer TC, that the first connecting element C1 in the first mounting region B1 has a rotation angle-stabilizing mechanism, and that the first connecting element C1 in the second mounting region B2 has a tilt angle-stabilizing mechanism.

The rotation angle-stabilizing mechanism has at least one friction contact. The at least one friction contact of the rotation angle-stabilizing mechanism is formed by the annular disk F11 with the part C1S of the first connecting element C1 and/or with the part C1R of the first connecting element C1.

The part C1S of the first connecting element C1 is permanently arranged on the stationary support frame 21 of the gantry 20. The part C1R of the first connecting element C1 is mounted so it can rotate by way of the first mounting region B1 about the first axis of rotation AV1 relative to the stationary support frame 21 of the gantry 20 and is connected to the frame element FE by way of the second mounting region B2.

The annular disk F11 forms a friction partner of the at least one friction contact of the rotation angle-stabilizing mechanism, is annularly arranged about the first axis of rotation AV1 and produced from plastics material. The annular disk F11 can optionally be permanently arranged, for example glued and/or connected with positive fit, either to the part C1S of the first connecting element C1 or to the part C1R of the first connecting element C1, in particular in relation to a rotation about the first axis of rotation AV1. The annular disk F11 has an arcuate hole which corresponds with the channel TR. The pin PN extends through the arcuate hole of the annular disk F11.

As an alternative to the annular disk F11, which has an arcuate hole, two or more annular disks can be used which are arranged concentrically around the first axis of rotation AV1. In particular, an annular gap can be located between two annular disks arranged concentrically around the first axis of rotation AV1, with an arcuate section of the annular gap corresponding to the channel TR. The pin PN can therefore extend through the arcuate section of the annular gap.

The tilt angle-stabilizing mechanism has a first friction contact and a second friction contact.

The first friction contact of the tilt angle-stabilizing mechanism is formed by the annular disk F21 with the part C1T of the first connecting element C1 and/or with the piston element SPB.

The annular disk F21 forms a friction partner of the first friction contact of the tilt angle-stabilizing mechanism, is annularly arranged about the first tilt axis AH1 and produced from plastics material. The annular disk F21 can optionally be permanently arranged, for example glued and/or connected with positive fit, either to the part C1T of the first connecting element C1 or to the piston element SPB, in particular in relation to a rotation about the first tilt axis AH1.

The second friction contact of the tilt angle-stabilizing mechanism is formed by the annular disk F22 with the part C1T of the first connecting element C1 and/or with the part C1R of the first connecting element C1. The part C1T of the first connecting element C1 is permanently arranged on the frame element FE.

The annular disk F22 forms a friction partner of the second friction contact of the tilt angle-stabilizing mechanism, is annularly arranged about the first tilt axis AH1 and produced from plastics material. The annular disk F22 can optionally be permanently arranged, for example glued and/or connected with positive fit, either to the part C1T of the first connecting element C1 or to the part C1R of the first connecting element C1, in particular in relation to a rotation about the first tilt axis AH1.

The tilt angle-stabilizing mechanism has a tensioning element SP in the form of a spring, whose windings are arranged around the first tilt axis AH1. The piston element SPB is arranged at a first end of the tensioning element SP. The tensioning element SP is arranged with a second end of the tensioning element SP on the part C1T of the first connecting element C1.

The second mounting region B2 has a bearing housing B2H. The bearing housing B2H is connected to the part C1R of the first connecting element C1 by way of the weld seam WS. The bearing housing B2H is designed to absorb forces and moments, which act on the frame element FE, and transfer them to the part C1R of the first connecting element C1. The bearing housing B2H has a hole. The part C1T of the first connecting element C1 extends through the hole in the bearing housing B2H. The part C1T of the first connecting element C1 is fixed with a fixing element relative to the bearing housing B2H at the side which faces away from the piston element FEN in relation to the bearing housing B2H. The fixing element is a nut FEN which is screwed with a thread of the first part C1T of the first connecting element C1. The bearing housing B2H, the annular disk F21 and the annular disk F22 are located between the nut FEN and the piston element SPB and are pressed together by the nut FEN and the piston element SPB.

The tensioning element SP generates a mechanical tension, in particular a strain tension, with which the first end of the tensioning element SP and the second end of the tensioning element SP are pressed apart. In this way the piston element SPB is pressed onto the annular disk F21 and the nut FEN pressed onto the annular disk F22.

The part C1T of the first connecting element C1 is permanently connected to the frame element FE at least in relation to the tilting movement of the frame element FE about the first tilt axis AH1. The embodiment shown in FIG. 9 provides that the part C1T of the first connecting element C1, the tensioning element SP, the piston element SPB, the annular disk F21 and the annular disk F22 together follow the tilting movement of the frame element FE about the first tilt axis AH1.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system for contrast agent-based medical imaging, comprising:
   a gantry of a medical imaging device;
   a contrast agent injection device; and
   a support arm including a frame element, a first connecting element and a second connecting element,
   wherein the frame element is connected to a stationary support frame of the gantry via the first connecting element such that at least part of the frame element is mounted to be movable relative to the stationary support frame of the gantry, and wherein the contrast agent injection device is connected to at least part of the frame element via the second connecting element such that the contrast agent injection device is mounted to be movable relative to at least part of the frame element, wherein at least one of
   the first connecting element includes a first mounting region,
   the frame element is mounted by way of the first mounting region so as to be rotatable about a first axis of rotation relative to the stationary support frame of the gantry, and
   the first connecting element includes a second mounting region, wherein the frame element is mountable by way of the second mounting region so as to be tiltable about a first tilt axis relative to the stationary support frame of the gantry.

2. The system of claim 1, wherein at least one of
the second connecting element includes a first connecting region in which the contrast agent injection device is connectable to the second connecting element, and
the second connecting element includes a second connecting region in which an additional component is connectable to the second connecting element, while the contrast agent injection device is connected to the second connecting element in the first connecting region.

3. The system of claim 2, wherein at least one of
the frame element is connected to the stationary support frame of the gantry via the first connecting element such that the frame element is mounted to be at least one of
rotatable about a first axis of rotation relative to the stationary support frame of the gantry and
tiltable about a first tilt axis;
the contrast agent injection device is connected to the frame element via the second connecting element such that the contrast agent injection device is mounted to be at least one of
rotatable about a second axis of rotation relative to the frame element and
tiltable about a second tilt axis; and
the additional component is connected to the frame element via the second connecting element such that the additional component is mounted to be at least one of
rotatable about the second axis of rotation relative to the frame element and
tillable about at least one of the second tilt axis and a third tilt axis.

4. The system of claim 2, wherein at least one of
the contrast agent injection device is at least one of positively and detachably connected to the second connecting element and
the additional component is at least one of positively and detachably connected to the second connecting element.

5. The system of claim 2, wherein the first connecting region and second connecting region are arranged symmetrically in relation to a second axis of rotation.

6. The system of claim 2, wherein the additional component includes at least one of a touch-sensitive screen and a tablet computer.

7. The system of claim 2, wherein the support frame includes a cavity which extends along the support frame such that a cable is arrangable in the cavity, and wherein the cable extends inside the cavity from the first connecting element to the second connecting element.

8. The system of claim 7, further comprising:
a cable, extending inside the cavity from an interior of the stationary support frame of the gantry to at least one of the contrast agent injection device and the additional component.

9. The system of claim 1, wherein at least one of
the first connecting element in the first mounting region includes a rotation-limiting mechanism for limiting the rotation of the frame element about the first axis of rotation to a specific rotation angle range and
the first connecting element in the second mounting region includes a tilting movement-limiting mechanism for limiting the tilting movement of the frame element about the first tilt axis to a specific tilt angle range.

10. The system of claim 9, wherein the rotation-limiting mechanism includes a channel in the form of an arc and a pin guided in the channel, and wherein the rotation of the frame element about the first axis of rotation is coupled to a movement of the pin along the channel and is limited to a rotation angle range encompassed by the channel.

11. The system of claim 1, wherein at least one of
the first connecting element in the first mounting region includes a rotation angle-stabilizing mechanism for stabilizing a rotation angle of the frame element in relation to a rotation of the frame element about the first axis of rotation and
the first connecting element in the second mounting region includes a tilt angle-stabilizing mechanism for stabilizing a tilt angle of the frame element in relation to a tilting movement of the frame element about the first tilt axis.

12. The system of claim 11, wherein the rotation angle-stabilizing mechanism has at least one friction contact, wherein the rotation of the frame element about the first axis of rotation is coupled to friction at the at least one friction contact of the rotation angle-stabilizing mechanism, and wherein the rotation angle is stabilizable by way of static friction at the at least one friction contact of the rotation angle-stabilizing mechanism.

13. The system of claim 11, wherein the tilt angle-stabilizing mechanism has at least one friction contact, wherein the tilting movement of the frame element about the first tilt axis is coupled to friction at the at least one friction contact of the tilt angle-stabilizing mechanism, and wherein the tilt angle is stabilizable by way of the static friction at the at least one friction contact of the tilt angle-stabilizing mechanism.

14. The system of claim 13, wherein at least one of
at least one friction partner of the at least one friction contact of the rotation angle-stabilizing mechanism is at least one of arranged at least one of annularly and in the manner of an arc about the first axis of rotation and is produced from plastics material; and
at least one friction partner of the at least one friction contact of the tilt angle-stabilizing mechanism is at least one of arranged at least one of annularly and in the manner of an arc about the first tilt axis and is produced from plastics material.

15. The system of claim 13, wherein at least one of
the rotation angle-stabilizing mechanism includes a tensioning element to cooperate with the at least one friction contact of the rotation angle-stabilizing mechanism such that the contact pressure underlying the friction at the at least one friction contact of the rotation angle-stabilizing mechanism is caused at least partly by a mechanical tensioning of the tensioning element of the rotation angle-stabilizing mechanism, and
the tilt angle-stabilizing mechanism includes a tensioning element to cooperate with the at least one friction contact of the tilt angle-stabilizing mechanism such that the contact pressure underlying the friction at the at least one friction contact of the tilt angle-stabilizing mechanism is caused at least partly by a mechanical tensioning of the tensioning element of the tilt angle-stabilizing mechanism.

16. The system of claim 15, wherein at least one of
the tensioning element of the rotation angle-stabilizing mechanism at least one of includes a spring and the spring of the tensioning element of the rotation angle-stabilizing mechanism includes one or more windings arranged around the first axis of rotation, and
the tensioning element of the tilt angle-stabilizing mechanism at least one of includes a spring and the spring of the tensioning element of the tilt angle-stabilizing mechanism includes one or more windings arranged around the first tilt axis.

17. The system of claim 3, wherein at least one of the first axis of rotation is vertical and the first tilt axis is horizontal.

18. The system of claim 3, wherein at least one of the second axis of rotation is vertical and the second tilt axis is horizontal at least for a tilt angle of the frame element in relation to a tilting movement of the frame element about the first tilt axis.

19. The system of claim 1, wherein at least one of
the frame element is connected to the stationary support frame of the gantry via the first connecting element such that the frame element is mounted to be at least one of
rotatable about a first axis of rotation relative to the stationary support frame of the gantry and
tiltable about a first tilt axis; and
the contrast agent injection device is connected to the frame element via the second connecting element such that the contrast agent injection device is mounted to be at least one of
rotatable about a second axis of rotation relative to the frame element and
tiltable about a second tilt axis.

20. The system of claim 1, wherein the contrast agent injection device is at least one of positively and detachably connected to the second connecting element.

21. The system of claim 1, wherein the support frame includes a cavity which extends along the support frame such that a cable is arrangable in the cavity, and wherein the cable extends inside the cavity from the first connecting element to the second connecting element.

22. The system of claim 21, further comprising:
a cable, extending inside the cavity from an interior of the stationary support frame of the gantry to the contrast agent injection device.

23. The system of claim 12, wherein at least one friction partner of the at least one friction contact of the rotation angle-stabilizing mechanism is at least one of arranged at least one of annularly and in the manner of an arc about the first axis of rotation and is produced from plastics material.

24. The system of claim 14, wherein at least one of
the rotation angle-stabilizing mechanism includes a tensioning element to cooperate with the at least one friction contact of the rotation angle-stabilizing mechanism such that the contact pressure underlying the friction at the at least one friction contact of the rotation angle-stabilizing mechanism is caused at least partly by a mechanical tensioning of the tensioning element of the rotation angle-stabilizing mechanism, and
the tilt angle-stabilizing mechanism includes a tensioning element to cooperate with the at least one friction contact of the tilt angle-stabilizing mechanism such that the contact pressure underlying the friction at the at least one friction contact of the tilt angle-stabilizing mechanism is caused at least partly by a mechanical tensioning of the tensioning element of the tilt angle-stabilizing mechanism.

25. The system of claim 24, wherein at least one of
the tensioning element of the rotation angle-stabilizing mechanism at least one of includes a spring and the spring of the tensioning element of the rotation angle-stabilizing mechanism includes one or more windings arranged around the first axis of rotation, and
the tensioning element of the tilt angle-stabilizing mechanism at least one of includes a spring and the spring of the tensioning element of the tilt angle-stabilizing mechanism includes one or more windings arranged around the first tilt axis.

26. A system for contrast agent-based medical imaging, comprising:
a gantry of a medical imaging device;
a contrast agent injection device; and
a support arm including a frame element, a first connecting element and a second connecting element,
wherein the frame element is connected to a stationary support frame of the gantry via the first connecting element such that at least part of the frame element is mounted to be movable relative to the stationary support frame of the gantry, and wherein the contrast agent injection device is connected to at least part of the frame element via the second connecting element such that the contrast agent injection device is mounted to be movable relative to at least part of the frame element,
wherein at least one of
the frame element is connected to the stationary support frame of the gantry via the first connecting element such that the frame element is mounted to be at least one of
rotatable about a first axis of rotation relative to the stationary support frame of the gantry and
tiltable about a first tilt axis; and
the contrast agent injection device is connected to the frame element via the second connecting element such that the contrast agent injection device is mounted to be at least one of
rotatable about a second axis of rotation relative to the frame element and
tiltable about a second tilt axis, and wherein the first axis of rotation is vertical and the first tilt axis is horizontal.

27. The system of claim 19, wherein at least one of the second axis of rotation is vertical and the second tilt axis is horizontal at least for a tilt angle of the frame element in relation to a tilting movement of the frame element about the first tilt axis.

28. The system of claim 26, wherein at least one of
the second connecting element includes a first connecting region in which the contrast agent injection device is connectable to the second connecting element, and
the second connecting element includes a second connecting region in which an additional component is connectable to the second connecting element, while the contrast agent injection device is connected to the second connecting element in the first connecting region, and wherein at least one of
the frame element is connected to the stationary support frame of the gantry via the first connecting element such that the frame element is mounted to be at least one of
rotatable about a first axis of rotation relative to the stationary support frame of the gantry and
tiltable about a first tilt axis;
the contrast agent injection device is connected to the frame element via the second connecting element such that the contrast agent injection device is mounted to be at least one of
rotatable about a second axis of rotation relative to the frame element and
tiltable about a second tilt axis; and
the additional component is connected to the frame element via the second connecting element such that the additional component is mounted to be at least one of rotatable about the second axis of rotation relative to the frame element and tiltable about at least one of the second tilt axis and a third tilt axis.

29. The system of claim 26, wherein at least one of the first connecting element includes a first mounting region, the frame element is mounted by way of the first mounting region so as to be rotatable about a first axis of rotation relative to the stationary support frame of the gantry, and the first connecting element includes a second mounting region, wherein the frame element is mountable by way of the second mounting region so as to be tiltable about a first tilt axis relative to the stationary support frame of the gantry.

30. The system of claim 29, wherein at least one of the first connecting element in the first mounting region includes a rotation-limiting mechanism for limiting the rotation of the frame element about the first axis of rotation to a specific rotation angle range and the first connecting element in the second mounting region includes a tilting movement-limiting mechanism for limiting the tilting movement of the frame element about the first tilt axis to a specific tilt angle range.

* * * * *